(12) United States Patent
Aguilar et al.

(10) Patent No.: US 8,138,132 B2
(45) Date of Patent: Mar. 20, 2012

(54) ADDITIVE COMPOSITION FOR EP GREASES WITH EXCELLENT ANTIWEAR AND CORROSION PROPERTIES

(75) Inventors: Gaston A Aguilar, Milford, CT (US); Ronald J Hiza, Monroe, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 251 days.

(21) Appl. No.: 12/332,891

(22) Filed: Dec. 11, 2008

(65) Prior Publication Data
US 2009/0156444 A1 Jun. 18, 2009

Related U.S. Application Data

(60) Provisional application No. 61/013,771, filed on Dec. 14, 2007.

(51) Int. Cl.
*C10M 135/36* (2006.01)
*C10M 137/10* (2006.01)
(52) U.S. Cl. .......... 508/274; 508/368; 508/371
(58) Field of Classification Search .......... 508/274, 508/368, 371
See application file for complete search history.

(56) References Cited

U.S. PATENT DOCUMENTS

| | | | |
|---|---|---|---|
| 5,487,837 A * | 1/1996 | Ozaki et al. | 508/162 |
| 5,736,493 A | 4/1998 | Garmier | |
| 6,300,291 B1 | 10/2001 | Hartley et al. | |
| 6,365,557 B1 * | 4/2002 | Karol et al. | 508/274 |
| 6,489,484 B1 | 12/2002 | Karol et al. | |
| 6,541,427 B1 | 4/2003 | Dresel | |
| 7,763,574 B2 * | 7/2010 | Donnelly et al. | 508/274 |
| 2004/0224859 A1 * | 11/2004 | Numazawa et al. | 508/364 |
| 2006/0035791 A1 * | 2/2006 | Donnelly et al. | 508/273 |
| 2007/0207934 A1 * | 9/2007 | Ozaki et al. | 508/168 |

* cited by examiner

*Primary Examiner* — Jim Goloboy
(74) *Attorney, Agent, or Firm* — Norris McLauglin & Marcus P.A.

(57) ABSTRACT

A lubricant composition is provided as follows:
At least 90% of a base grease;
(a) a thiadiazole poly(ether)glycol complex in an amount which provides about 1500 to 3500 ppm sulfur;
(b) molybdenum dihydrocarbyldithiophosphate in amount which provides about 77 to 450 ppm molybdenum; and
(c) zinc dihydrocarbyldithiophosphate in an amount which provides about 600 to 1000 ppm zinc. An additive composition for grease, consisting of components (a), (b) and (c), is also provided.

7 Claims, No Drawings

ADDITIVE COMPOSITION FOR EP GREASES WITH EXCELLENT ANTIWEAR AND CORROSION PROPERTIES

FIELD OF INVENTION

The present invention is directed to an additive composition for extreme pressure ("EP") grease compositions having exceptional antiwear and corrosion properties. More specifically, the invention relates to an additive composition comprising (A) thiadiazole poly(ether)glycol complex (B) molybdenum dihydrocarbyldithiophosphate and (C) zinc dihydrocarbyldithiophosphate.

BACKGROUND

EP greases lubricate under highly loaded conditions and require highly effective EP additives to prevent scoring and welding. Thiadiazoles are compounds that are effective EP additives. U.S. Pat. No. 6,365,557 discloses thiadiazole/poly (ether)glycol complexes. Although these complexes are excellent extreme pressure additives for greases, their high surface affinity to metals surfaces produces coatings that generate undesirable discoloration of copper and other non-ferrous metals and block the ability of antiwear additives to reduce wear. The invention herein teaches specific lubricant additive composition in which these thiadiazole poly(ether) glycol complexes do not have negative impact on wear and corrosion while maintaining the exceptional extreme pressure properties.

U.S. Pat. No. 6,541,427 (Dresel et al.) discloses a grease formulation having additive system that contains 2% molybdenum compound (dihydrocarbyldithiocarbamate, MoDTC or dihydrocarbyldithiophosphate MoDTP), about 2% thiadiazole derivative and requires an assortment of other additives.

SUMMARY OF THE INVENTION

The invention relates to a lubricant composition comprising the following components, all in weight %:
(a) Major amount (i.e. >90%) of base grease, such as lithium, lithium complex, aluminum complex, calcium complex organo-clay and polyurea.
(b) Thiadiazole poly(ether)glycol complex providing 1500 to 3500 ppm sulfur (S), preferably 2000 to 2800 ppm S;
(c) Molybdenum dihydrocarbyldithiophosphate providing 77 to 450 ppm molybdenum (Mo), preferably 192-220 ppm Mo;
(d) Zinc dihydrocarbyldithiophosphate providing 600 to 1000 ppm zinc (Zn), preferably 700 to 900 ppm Zn.

The invention also discloses an additive composition for use in grease. The additive composition is comprised of the following compounds:
(a) Thiadiazole poly(ether)glycol complex;
(b) Molybdenum dihydrocarbyldithiophosphate;
(c) Zinc dihydrocarbyldithiophosphate.
at the S:Mo:Zn weight ratio of about 150-350:7.7-45:60-100. In this ratio, the S refers to sulfur provided by the thiadiazole/poly(ether)glycol complex.

DETAILED DESCRIPTION OF THE INVENTION

Thiadiazole/poly(ether)glycol complexes of this invention are described in U.S. Pat. No. 6,365,557, incorporated herein by reference. Preferred embodiments comprise a complex of:
(a) one or more thiadiazole compound as follows:
(i) dimers of 2,5-dimercapto-1,3,4-thiadiazole (DMTD) having the formula:

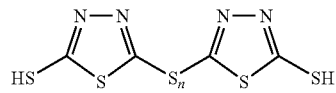

I wherein n is 1 and/or 2; and/or
(ii) 2-mercapto-1,3,4-thiadiazole (MTD) having formula:

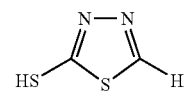

II and (b) poly(ether)glycol having formula:

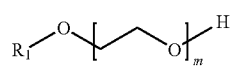

III wherein $R_1$ is hydrogen, a branched or straight chain $C_1$ to $C_{20}$ alkyl radical, a phenyl radical, a $C_1$ to $C_8$ branched straight chain acyl radical, and combination thereof, and m is 1 to 300. Preferred poly(ether)glycols are butoxytriglycol, polyethylene glycol or a combination thereof, with the latter combination being most preferred.

As set out above, the
(a) thiadiazole may be one or more of the mono sulfide dimer of DMTD (Formula I, n=1), disulfide dimer of DMTD (Formula I, n=2) and MTD (Formula II); and such is to be complexed with
(b) poly(ether)glycol (Formula III).

The complex may comprise, by weight, from about 10% to 60% thiadiazole compound(s) and about 40% to 90% poly(ether)glycol compound(s); preferably about 25% to 50% thiadiazole compound(s) and about 50% to 75% poly(ether) glycol compound(s); and most preferably about 30% to 40% thiadiazole and about 60% to 70% poly(ether)glycol.

A most preferred embodiment for the complex is available as Vanlube® 972M additive from R.T. Vanderbilt Company, Inc. of Norwalk, Conn. Vanlube 972M comprises approximately, by weight: (a) 15% of mono sulfide dimer of DMTD, 10% disulfide dimer of DMTD, 10% of MTD; and (b) 49% butoxytriglycol and 16% polyethylene glycol; and has an average molecular weight of 300 grams per mole.

Molybdenum and zinc dihydrocarbyldithiophosphate compounds are usually prepared by reacting $P_2S_5$ with alcohols to form dihydrocarbyldithiophosphoric acid compounds, which are then neutralized with suitable molybdenum or zinc compounds:

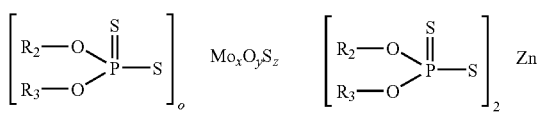

wherein $R_2$ and $R_3$ are independent hydrocarbyl groups containing 1 to 18 preferably 2 to 12 carbon atoms including alkyl, alkenyl, aryl, arylalkyl, alkylaryl and cycloaliphatic groups. Examples of hydrocarbyl groups are ethyl, n-propyl, isopropyl, n-butyl, isobutyl, sec-butyl, iso-octyl, 2-ethylhexyl, and butylphenyl. In the case of molybdenum dihydrocarbyldithiophosphate, o is 2 and 4; x is 1 to 2; y is 1 to 4; and z is 1 to 4.

Test Methods

Test methods used in this invention to evaluate extreme pressure, corrosion resistance, and wear properties of grease compositions were the following:
1. Timken EP Test
2. Copper Strip Test
3. 4-Ball Wear Test The Timken test is a well-known standardized test, and described in ASTM D 2509. The Timken test measures the loads at which abrasive wear, i.e. scoring, occur between a rotating cup and stationary block; thus, the higher the Timken OK load, the better the EP properties of the grease. An informal EP ranking based Timken OK load performance is provided below; wherein anything in the range 60-80 (excellent or exceptional) is considered acceptable to industry standards:

| Timken OK Load, (lb.) | EP Performance Ranking |
|---|---|
| 80 | Exceptional |
| 60-70 | Excellent |
| 50 | Good |
| 40 | Marginal |

Copper strip test method, ASTM D 4048, was used to evaluate copper corrosion characteristics of grease compositions. In this test method, the polished copper strip is totally immersed in a sample of grease and heated in an oven at 100° C. for 24 hours. At the end of this period, the strip is removed, washed, and compared with the ASTM Copper Strip Corrosion Standards. A copper strip is assigned a rating of 1a to 4b. A rating of 1a represents a strip with the least amount of corrosion and 4c represents a strip with the maximum amount of corrosion. Commercial greases are non-corrosive and produce ratings no higher than 1b.

Four-Ball Wear Tests are conducted according to standard procedure described in ASTM D4172. In this test method, one ball is rotated on three evenly spaced static balls while the four balls are completely submerged under the test oil. The tests for this invention were conducted at a rotation speed of 1200 rpm under a load of 40 kg for one hour at 75° C. The scar diameter of three static balls is measured and the result is the average of the three. An acceptable result for this test is an average wear scar that is less 0.5 mm in diameter.

Example 1

Lithium grease containing thiadiazole poly(ether)glycol complex (Vanlube® 972M additive available from R.T. Vanderbilt Company, Inc. of Norwalk, Conn.), Vanlube 972M in combination molybdenum dialkyldithiophosphate (Molyvan® L additive available from R.T. Vanderbilt Company, Inc.), Vanlube 972M in combination zinc dialkyldithiophosphate (Lubrizol® 1395, available from Lubrizol Corp.) diluted with 10-20% oil and Vanlube 972M in combination with Molyvan L and Lubrizol 1395, were evaluated for wear, EP and corrosion properties. The data as summarized Table 1 shows that only the greases treated with all three components and particular concentrations carried excellent to exceptional Timken OK loads with acceptable wear scars and copper corrosion ratings. In addition, data for formulation 10, 11, 12 and 13 indicate that other molybdenum compounds such molybdenum dialkyldithiocarbamates (Molyvan® 822) and organo-molybdates (Molyvan® 855) are not effective alternatives to MoDTP.

TABLE 1

| | 1 | 2 | 3 | 4 | 5 | 6 | 7 | 8 | 9 | 10 | 11 | 12 | 13 |
|---|---|---|---|---|---|---|---|---|---|---|---|---|---|
| Vanlube 972M[1] | 2.0 | 1.0 | 2.0 | 2.0 | 1.0 | 1.0 | 1.0 | 1.0 | 1.0 | 1.0 | 1.0 | 1.0 | 1.0 |
| Lubrizol 1395[2] | — | — | 1.0 | — | 1.0 | — | — | 0.50 | 0.75 | 0.75 | 0.75 | 0.75 | 0.75 |
| Molyvan L[3] | — | — | — | 1.0 | — | 1.0 | 0.5 | 0.25 | 0.25 | — | — | — | — |
| Molyvan 822[4] | — | — | — | — | — | — | — | — | — | 0.25 | 0.50 | — | — |
| Molyvan 855[5] | — | — | — | — | — | — | — | — | — | — | — | 0.25 | 0.50 |
| S Content, ppm | 4800 | 2400 | 4800 | 4800 | 2400 | 2400 | 2400 | 2400 | 2400 | 2400 | 2400 | 2400 | 2400 |
| Mo Content, ppm | 0 | 0 | 0 | 825 | 0 | 825 | 412 | 206 | 206 | 123 | 246 | 198 | 396 |
| Zn Content, ppm | 0 | 0 | 1060 | 0 | 1060 | 0 | 0 | 530 | 795 | 795 | 795 | 795 | 795 |
| 4-Ball Wear, mm | 0.64 | 0.58 | 0.61 | 0.52 | 0.53 | 0.46 | 0.44 | 0.47 | 0.46 | 0.52 | 0.51 | 0.48 | 0.53 |
| Timken OK Load, lb. | 80 | Fail 40 | — | — | — | — | 70 | 60 | 80 | Fail 40 | Fail 40 | Fail 40 | — |
| Copper corrosion | 2e | 2e | 4a | 2e | 3a | 4b | 2e | 3a | 1b | 1b | 1b | 1b | 1b |

[1]Sulfur content of Vanlube 972M is 24% (by weight).
[2]Zinc content of Lubrizol 1395 is 10.6 percent %.
[3]Molybdenum content of Molyvan L is 8.3%.
[4]Molybdenum content of Molyvan 822 is 4.9%.
[5]Molybdenum content of Molyvan 855 is 7.9%.

Example 2

Comparative Examples

As comparative examples, ZDDP component of the invention was substituted with other phosphorus and zinc based antiwear (AW) additives while keeping the other components of the invention constant. As summarized in Table 2, none of alternatives provided satisfactory antiwear performance with exception of zinc naphthenate. However, EP performance of zinc naphthenate containing composition was unsatisfactory.

TABLE 2

| (Comparative Examples) | | | | | | |
|---|---|---|---|---|---|---|
| | 14 | 15 | 16 | 17 | 18 | 19 |
| Vanlube 972M | 1.00 | 1.00 | 1.00 | 1.00 | 1.00 | 1.00 |
| Molyvan L | 0.25 | 0.25 | 0.25 | 0.25 | 0.25 | 0.25 |
| Vanlube 7611M (ashless dialkyldithiophosphate AW additive) | 0.75 | — | — | — | — | — |
| Vanlube 9123 (amine phosphate AW additive) | — | 0.75 | — | — | — | — |
| Vanlube 727 (ashless dialkyldithiophosphate AW additive) | — | — | 0.75 | — | — | — |
| Vanlube 672 (amine phosphate AW additive) | — | — | — | 0.75 | — | — |
| Vanlube AZ (50% zinc dialkyldithiocarbamate) | — | — | — | — | 1.30 | — |
| Zinc naphthenate | — | — | — | — | — | 0.75 |
| 4-Ball Wear, mm | 0.58 | 0.53 | 0.57 | 0.56 | 0.51 | 0.47 |
| Timken OK Load, lb | — | — | — | — | — | Fail 40 |
| Copper corrosion | — | — | — | — | 3a | 1b |

Example 3

Comparative Examples

For comparison, thiadiazole poly(ether)glycol complex component of the invention was exchanged with other thiadiazole derivatives. As summarized in Table 3, none of alternatives provided satisfactory EP performance:

TABLE 3

| (Comparative Examples) | | |
|---|---|---|
| | 20 | 21 |
| Lubrizol 1395 (ZDDP) | 0.75 | 0.75 |
| Molyvan L | 0.25 | 0.25 |
| Vanlube 829 (Thiadiazole disulfide dimer used at equivalent sulfur content as 1% Vanlube 972M) | 0.37 | — |
| Cuvan ® 826 (Thiadiazole derivative used at equivalent sulfur content as 1% Vanlube 972M) | — | 0.77 |
| 4-Ball Wear, mm | 0.43 | 0.44 |
| Timken OK Load, lb | 30 | 20 |
| Copper corrosion | 1b | 1b |

What is claimed is:

1. A lubricant composition comprising, in weight %:
   at least 90% of a lithium or lithium complex base grease; and
   (a) a thiadiazole poly(ether)glycol complex in an amount which provides about 2400 to 3500 ppm sulfur;
   (b) molybdenum dihydrocarbyldithiophosphate in amount which provides about 200 to 450 ppm molybdenum; and
   (c) zinc dihydrocarbyldithiophosphate in an amount which provides about 800 to 1000 ppm zinc.

2. The lubricant composition of claim 1, wherein the thiadiazole poly(ether)glycol complex comprises
   (a) one or more thiadiazole compound as follows:
      (i) dimers of 2,5-dimercapto-1,3,4-thiadiazole (DMTD) having the formula:

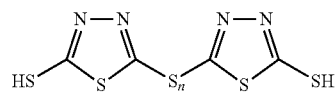

wherein n is 1 and/or 2; and/or
      (ii) 2-mercapto-1,3,4-thiadiazole (MTD) having formula:

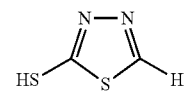

and (b) poly(ether)glycol having formula:

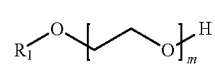

wherein $R_1$ is hydrogen, a branched or straight chain $C_1$ to $C_{20}$ alkyl radical, a phenyl radical, a $C_1$ to $C_8$ branched straight chain acyl radical, and combination thereof, and m is 1 to 300.

3. The lubricant composition of claim 2, wherein the thiadiazole poly(ether)glycol complex comprises, as weight percent of the complex: (a) the thiadiazole composition at about 10% to 60% and (b) the poly(ether)glycol composition at about 40% to 90%.

4. The lubricant composition of claim 2, wherein the poly (ether)glycol of the thiadiazole poly(ether)glycol complex comprises a combination of butoxytriglycol and polyethylene glycol.

5. The lubricant composition of claim 2, wherein thiadiazole comprises a combination of mono sulfide dimer of DMTD (Formula I, n=1), disulfide dimer of DMTD (Formula I, n=2) and MTD (Formula II).

6. The lubricant composition of claim 2, wherein the thiadiazole poly(ether)glycol complex comprises, as weight percent of the complex, about:
   (a) 15% of mono sulfide dimer of DMTD, 10% disulfide dimer of DMTD, 10% of MTD; and
   (b) 45% butoxytriglycol and 15% polyethylene glycol.

7. The lubricant composition of claim 6, wherein
(a) the thiadiazole poly(ether)glycol complex provides about 2400 ppm sulfur;
(b) the molybdenum dihydrocarbyldithiophosphate provides about 206 ppm molybdenum; and
(c) the zinc dihydrocarbyldithiophosphate provides about 795 ppm zinc.

* * * * *